United States Patent [19]

Buysch et al.

[11] 4,434,105

[45] Feb. 28, 1984

[54] PROCESS FOR THE PREPARATION OF DIALKYL CARBONATES

[75] Inventors: Hans-Josef Buysch; Heinrich Krimm; Hans Rudolph, all of Krefeld, Fed. Rep. of Germany

[73] Assignee: Bayer Aktiengesellschaft, Leverkusen, Fed. Rep. of Germany

[21] Appl. No.: 163,912

[22] Filed: Jun. 27, 1980

Related U.S. Application Data

[63] Continuation of Ser. No. 51,658, Jun. 25, 1979, abandoned.

[30] Foreign Application Priority Data

Oct. 29, 1977 [DE] Fed. Rep. of Germany ....... 2748718

[51] Int. Cl.$^3$ .................... C07C 68/00; C07C 69/96
[52] U.S. Cl. ...................................... 260/463; 568/867
[58] Field of Search ............................ 260/463, 340.2; 568/867

[56] References Cited

U.S. PATENT DOCUMENTS

| | | | |
|---|---|---|---|
| 2,773,070 | 12/1959 | Lichtenwalter et al. | 260/340.2 |
| 2,924,608 | 2/1960 | Mills | 260/340.2 |
| 2,994,704 | 8/1961 | Crosby et al. | 260/340.2 |
| 3,248,415 | 4/1966 | Stevens | 260/463 |
| 3,535,341 | 10/1970 | Emmons et al. | 260/340.2 |
| 3,535,342 | 10/1970 | Emmons | 260/340.2 |
| 3,642,858 | 2/1972 | Frevel et al. | 260/463 |
| 3,896,090 | 7/1975 | Maximovich | 260/463 |
| 4,181,676 | 1/1980 | Buysch et al. | 260/463 |

FOREIGN PATENT DOCUMENTS

2615665  10/1976  Fed. Rep. of Germany ...... 260/463

*Primary Examiner*—Mary C. Lee
*Attorney, Agent, or Firm*—Sprung, Horn, Kramer & Woods

[57] ABSTRACT

A process for preparing a dialkyl carbonate which comprises contacting an alkylene oxide with an aliphatic or cycloaliphatic alcohol and carbon dioxide in the presence of a catalyst at an elevated temperature.

9 Claims, No Drawings

PROCESS FOR THE PREPARATION OF DIALKYL CARBONATES

This is a continuation, of application Ser. No. 051,658, filed June 25, 1979 now abandoned.

BACKGROUND OF THE INVENTION

1. Field of the Invention

The invention relates to a process for the preparation of dialkyl carbonates by reacting alkylene oxides with alcohols and carbon dioxide in the presence of catalysts.

2. Discussion of the Prior Art

It is surprising that dialkyl carbonates can be prepared at all by reacting alkylene oxides with alcohols and carbon dioxide.

Rather, it was to be expected that polymerisation reactions which lead, for example, to polycarbonates and polyglycols take place in the reaction of alkylene oxides with alcohols and carbon dioxide.

It is known, in fact, from U.S. Pat. Nos. 3,248,415 and 3,248,416 that alkylene oxides and carbon dioxide or alkylene oxides, carbon dioxide and glycol carbonates react in the presence of small amounts of diglycols or polyglycols, under the catalytic influence of bases, to give polycarbonates which, however, predominantly contain polyalkylene oxide units and therefore in the strict sense are to be considered polyether-polycarbonates.

Furthermore, it is known from Makromol. Chem. 130, 210 (1969) that in the reaction of alkylene oxides with carbon dioxide in the presence of zinc diethyl as the catalyst, large amounts of polyglycols are obtained in addition to small amounts of alternating copolymers of alkylene oxides and carbon dioxide.

In addition to the polymerisation reactions, the formation of alkyl glycol ethers was to be expected as a side reaction. Because of the large number of hydroxyl groups present, amounts of alcohols equivalent to the amounts of alkylene oxide are added. Thus, the alkylene oxide should react with the alcohol to a considerable degree to give alkyl glycol ethers.

SUMMARY OF THE INVENTION

It has now been found that dialkyl carbonates can be prepared in good yields if alkylene oxides are reacted with aliphatic and/or cycloaliphatic alcohols and carbon dioxide in the presence of catalysts at elevated temperature.

Possible aliphatic and/or cycloaliphatic alcohols, e.g. alkanols and cycloalkanols are those with 1 to 18, preferably with 1 to 12, carbon atoms. Examples which may be mentioned are: methanol, ethanol, propanol, isopropanol, n-butanol, isobutanol, amyl alcohol, cyclohexanol, octanol, decanol and cyclododecanol.

Alkylene oxides which are employed in the process according to the invention are those with 2 to 8, preferably with 2 to 3, carbon atoms. Examples which may be mentioned are: vinyloxirane, epichlorohydrin, 1,2- and 2,3-butylene oxide, cyclohexene oxide, ethylene oxide and propylene oxide; ethylene oxide and propylene oxide are preferably employed.

Suitable catalysts for the process according to the invention include basic organic nitrogen compounds, in particular tertiary amines, e.g. tertiary alkyl, tertiary alkylene, tertiary hydroxy alkyl and tertiary hydroxy alkylene, tertiary aryl and tertiary amino having both aliphatic and aromatic groups attached to the nitrogen atom. These include amines with 3 to 18, preferably with 3 to 12, carbon atoms. Examples which may be mentioned are: triethylamine, tributylamine, triethanolamine, dimethylbenzylamine and dimethylstearylamine.

Furthermore, heterocyclic aromatic nitrogen compounds with 2 to 15, preferably with 2 to 12, carbon atoms are suitable. Examples which may be mentioned are pyridine, pyrimidine, imidazole, triazole, tetrazole, benzimidazole, benztriazole and benzthiazole.

Hydrazines such as hydrazine itself, dimethylhydrazine and dibenzylhydrazine as well as amidines, such as formamidine and acetamidine, cyclic amidines, such as 2-alkyl-imidazol-2-ines, guanidine and urea can also be used as catalysts. In addition, the salts of all the nitrogen compounds mentioned with weak and strong acids, such as carboxylic acids with 1 to 18 carbon atoms, carboxylic acid or hydrogen halide acids, as well as quaternization products of the nitrogen compounds mentioned, for example those which are obtained by reacting the nitrogen compounds with alkylating agents, for example alkyl halides, can be employed as catalysts. Examples of such compounds are tetramethylammonium bromide or iodide, tetrabutylammonium chloride, dimethylpiperidinium iodide, N-methyl-pyridinium bromide, N,N'-dimethylimidazolium chloride and N-methyl-benzthiazolium iodide.

Other salt-like compounds, such as the sulphonium and phosphonium salts of hydrogen halide acids, for example triethylsulphonium iodide, tetraethylphosphonium bromide, tetrabutylphosphonium iodide and triphenyl-benzyl-phosphonium chloride, are also suitable catalysts.

A further class of substances having a catalytic action comprises the oxides, hydroxides and salts of the alkali metals and alkaline earth metals, such as LiOH, LiCl, $Li_2CO_3$, NaOH, NaOAc, $K_2CO_3$, NaI, KBr, K stearate, Sr stearate, $CaCl_2$ and $CaI_2$, and furthermore the oxides, hydroxides, carbonates and hydrogen halide acid salts of heavy metals (In, Cd, Co, Fe, Ni, Mn, Pb, for example) such as $ZnCl_2$, $CdI_2$, $CoBr_2$, $FeCl_3$, $NiCl_2$, $MnI_2$, $CoCo_3$ and $PbCl_2$, and compounds of tin, above all also with organic radicals with up to 46 carbon atoms, such as $SnCl_2$, $(But)_2SnO$, $(But)_2Sn(laurate)_2$, $(But)_2Sn(OCH_3)Hd$ 2, $Na_2SnO_2$ and $Na_2SnO_3$, and finally the oxides, hydroxides and salts of thallium with inorganic and organic acids, such as $Tl_2CO_3$, $Tl_2O$, TlOAc, $TlNO_3$, $Tl(OAc)_3$, $Tl_2O_3$ and TlI. In some cases it proves favorable to use a combination of the catalysts mentioned, such as $NaI/Tl_2CO_3$, $NaI/Li_2CO_3$, $CoCo_3/TlI$ or N-methylpyridinium bromide/guanidine carbonate, or to first produce the catalyst in the reaction mixture, for example by employing triethylamine and ethyl iodide.

The catalysts can also be applied to solid supports, for example to MgO and $Al_2O_3$, or can be used in the form of solid catalysts, for example as polystyrenes which are crosslinked with divinyl benzene and contain amino groups or quaternary ammonium groups.

The halides, alcoholates, oxides, hydroxides and carbonates of the alkali metals and of thallium and the halides of quaternary ammonium bases, in particular the bromides and iodides, are preferably used as catalysts. It is very advantageous to use mixtures of these compounds, in particular those which contain thallium compounds.

The molar ratio of the alkylene oxide to alcohol is not critical in the process according to the invention. It is usually in the range from about 1:1 to 1:20, preferably 1:2 to 1:15. However, the molar ratio can also be outside the range indicated. In general, an excess of alcohol is preferably employed in order to shift the reaction equilibrium in the direction of the desired dialkyl carbonates.

Carbon dioxide is usually employed in an excess of 0.1 to 100 mols/mol of ethylene oxides. The partial pressure of carbon dioxide should be in the range from about 1 to 1,000 bars here, preferably 3 to 500 bars and particularly preferably 5 to 200 bars.

The reaction temperatures of the process according to the invention are in general about 70° to 300° C., preferably 90° to 280° C. and particularly preferably 100° to 250° C.

The reaction can be carried out discontinuously or continuously, for example in a tube reactor. The reaction components are separated by customary methods, for example by fractional distillation. The catalyst remaining in the residue can be reused.

The dialkyl carbonates can be obtained in yields of over 97% of theory by the process according to the invention.

The products of the process according to the invention are suitable as solvents for cellulose derivatives and as starting materials for the preparation of diaryl carbonates, aliphatic and aromatic polycarbonates, medicaments and plant protection agents (DT-OS (German Published Specification) No. 2,528,412, DT-AS (German Published Specification) No. 1,031,512, U.S. Pat. No. 3,933,846, J. Amer. Chem. Soc. 52, 314 (1930) and Ullmann's Encyclopädie der technischen Chemie, (Ullmann's Encyclopaedia of industrial Chemistry), 3rd edition, volume 9, page 776 et seq. (1957)).

The examples which follow are intended to illustrate the process according to the invention in more detail, but without limiting it to these examples.

EXAMPLE 1

A mixture of 640 g (20 mols) of methanol and 44 g (1 mol) of ethylene oxide is kept at 120° C. in the presence of 1 g of sodium iodide and 0.2 g of thallium carbonate under a $CO_2$ pressure of 70 bars for 2 hours. After cooling, the mixture is let down.

The gas chromatogram of the reaction mixture shows that about 7% by weight of dimethyl carbonate is present in the reaction mixture. The diglycol content is about 0.3% by weight, the triglycol content is 0.1% by weight and the methylglycol content is 0.5% by weight.

Working up the reaction mixture by distillation gives, in addition to the methanol fraction containing 51 g of dimethyl carbonate, 49 g of a fraction which boils at 60°–80° C./0.8 mm Hg and consists of about 30 g of glycol and 19 g of glycol carbonate. The residue is 1.8 g and virtually corresponds to the amounts of catalyst employed.

EXAMPLE 2

Example 1 is repeated. Following the reaction (2 hours at 150° C. under a pressure of 88 bars of $CO_2$), after cooling, the $CO_2$ is allowed to escape and the temperature is kept at 150° C. for a further 2 hours.

According to the gas chromatogram, the reaction mixture contains 0.1% of diglycol and triglycol and about 0.7% of methylglycol. After working up as in Example 1, a methanol fraction consisting of 85 g of dimethyl carbonate and a glycol fraction which contains 3–4 g of glycol carbonate are obtained. The distillation residue is 2.5 g.

The ethylene oxide employed is thus converted to the extent of over 94% into glycol, and an equivalent proportion of methanol and $CO_2$ is converted into dimethyl carbonate. The glycol carbonate formed can be converted into dimethyl carbonate by trans-esterification, so that the total yield of dimethyl carbonate, relative to ethylene oxide employed, is then >97% of theory.

EXAMPLE 3

A mixture of 640 g (20 mols) of methanol, 53 g (1.2 mols) of ethylene oxide, 2 g of sodium iodide and 0.2 g of thallium hydroxide is kept at 160° C. under 100 bars of $CO_2$ for 2 hours, the $CO_2$ is blown out and the mixture is kept at 150° C. for a further ½ hour. After working up by distillation, a methanol fraction which contains 102 g of dimethyl carbonate and about 1 g of methylglycol is obtained. The distillation residue is 3 g and thus virtually corresponds to the amount of catalyst.

EXAMPLE 4

A mixture as in Example 1, which contains 1 g of sodium iodide as the catalyst and no thallium salt, is reacted at 150° C. for 2 hours. The methanol fraction which has been separated off by distillation contains 57 g of dimethyl carbonate and 0.2 g of methylglycol. The sodium iodide employed remains as a distillation residue of 1 g. Ethylene oxide is not quantitatively converted.

EXAMPLE 5

A mixture as in Example 1 is reacted in the presence of 1 g of lithium hydroxide under a $CO_2$ pressure of 50 bars at 150° C. for 2 hours. With incomplete conversion of ethylene oxide after working up, 45 g of dimethyl carbonate and 0.3 g of methylglycol are obtained in the methanol fraction. The residue is 1.5 g.

EXAMPLE 6

A mixture as in Example 1 is allowed to react in the presence of 1 g of triethanolamine as the catalyst at 150° C. and under a $CO_2$ pressure of 30 bars for 2 hours. With incomplete conversion of the ethylene oxide, 33 g of dimethyl carbonate and 0.5 g of methylglycol are obtained in the methanol fraction. The residue is 2.5 g.

EXAMPLE 7

A mixture as in Example 1 is heated to 150° C. in the presence of 0.2 g of sodium carbonate as the catalyst under a $CO_2$ pressure of 80 bars for 2 hours. The methanol fraction which has been separated off contains 23 g of dimethyl carbonate and 0.5 g of methylglycol. 1.5 g remain as the residue.

EXAMPLE 8

A mixture as in Example 1 is heated to 150° C. in the presence of 0.1 g of sodium iodide as the catalyst under a $CO_2$ pressure of 80 bars for 2 hours. 19 g of dimethyl carbonate and 0.6 g of methylglycol are obtained in the methanol fraction.

EXAMPLE 9

A mixture as in Example 1 is heated to 150° C. in the presence of 1 g of imidazole as the catalyst under a $CO_2$ pressure of 20–30 bars for 2 hours. The yield of dimethyl carbonate is 18 g.

EXAMPLE 10

A mixture as in Example 1 is heated to 150° C. in the presence of 1 g of 1,5-diazabicyclo-(0,4,5)-undec-5-ene as the catalyst under a $CO_2$ pressure of 80 bars for 2 hours. The yield of dimethyl carbonate is 16 g.

EXAMPLE 11

Example 1 is repeated at 150° with 0.5 g of tetraethylammonium bromide as the catalyst. The yield of dimethyl carbonate is 25 g.

EXAMPLE 12

If Example 10 is repeated with 0.5 g of tetrabutylammonium iodide as the catalyst, 28 g of dimethyl carbonate are obtained.

EXAMPLE 13

A mixture of 640 g (20 mols) of methanol and 132 g (3 mols) of ethylene oxide is kept at 150° C. in the presence of 1 g of sodium iodide and 0.2 g of thallium hydroxide under a $CO_2$ pressure of 110 bars for 2 hours. With incomplete conversion of the ethylene oxide, 123 g of dimethyl carbonate and 0.6 g of methylglycol are obtained in the methanol fraction. 2 g remain as the residue.

EXAMPE 14

Example 1 is repeated at 150° C. with 1 g of lithium methylate as the catalyst. The yield of dimethyl carbonate is 53 g.

EXAMPLE 15

Example 1 is repeated with 1 g of guanidine carbonate as the catalyst. The yield of dimethyl carbonate is 11 g.

EXAMPLE 16

Example 1 is repeated with 1 g of lithium iodide as the catalyst. The yield of dimethyl carbonate is 56 g.

EXAMPLE 17

Example 1 is repeated with 2 g NaJ and 0,2 g $Tl_2CO_3$ under the conditions of example 1. The yield of dimethyl carbonate is 78 g.

EXAMPLE 18

A mixture of 796 g (17.3 mols) of ethanol and 36 g (0.82 mol) of ethylene oxide is reacted with one another under the conditions of Example 1.

The yield of diethyl carbonate is 22 g, corresponding to a conversion of the ethylene oxide employed of 23%. Ethylglycol is not found. The distillation residue is 2 g and thus corresponds to the amount of catalyst employed.

EXAMPLE 19

If Example 18 is repeated with 1 g of imidazole instead of the catalyst from Example 1 and the mixture is kept at 200° C. under a $CO_2$ pressure of 88 bars for 2 hours, an amount of diethyl carbonate which corresponds to a conversion of the ethylene oxide employed of 43% is obtained.

EXAMPLE 20

A mixture of 749 g (16.3 mols) of ethanol and 45 g (0.775 mol) of propylene oxide is kept under a $CO_2$ pressure of 80 bars and in the presence of 0.18 g of thallium carbonate and 1.8 g of sodium iodide at 150° C. for 2 hours. After blowing out the $CO_2$, the mixture is kept at 200° C. for a further 2 hours. The yield of diethyl carbonate is 76 g, corresponding to a conversion of propylene oxide of 83%. Ethylether of Propylenglycol has not formed. The amount of residue from the distillation corresponds to the amount of catalyst employed.

EXAMPLE 21

Example 1 is repeated with 88 g (2.0 mols) of $CO_2$, corresponding to a molar ratio of $CO_2$ to ethylene oxide of 2:1. After 2 hours at 150° C. a yield of 65 g of dimethyl carbonate are obtained.

EXAMPLE 22

If EXAMPLE 21 is repeated with 52 g (1,2 mol) of $CO_2$, corresponding to a molar ratio of $CO_2$ to ethylene oxide of 1,2:1, 68 g of dimethyl carbonate are obtained. The distillation residue is 2 g.

What is claimed is:

1. A process for preparing a carbonate which comprises contacting an alkylene oxide having 2 to 8 carbon atoms with an aliphatic or cycloaliphatic alcohol having 1 to 18 carbon atoms selected from the group consisting of methanol, ethanol, propanol, isopropanol, n-butanol, isobutanol, amyl alcohol, cyclohexanol, octanol, decanol, and cyclododecanol and excess carbon dioxide under a partial carbon dioxide pressure of 3 to 500 bars employing excess alcohol to alkylene oxide in the presence of a catalyst which is a thallium catalyst at a temperature of from 70° to 300° C.

2. A process according to claim 1 wherein the reaction is carried out at a temperature in the range of from 100° to 250° C.

3. A process according to claim 1 wherein the process is carried out under a partial carbon dioxide pressure of 5 to 200 bars.

4. A process according to claim 1 wherein the alkylene oxide is ethylene oxide or propylene oxide.

5. A process according to claim 1, wherein the process is carried out employing a reaction mixture consisting essentially of said alkylene oxide, said aliphatic or cycloaliphatic alcohol, said carbon dioxide and said catalyst.

6. A process according to claim 1, wherein said thallium catalyst is $Tl_2CO_3$, $Tl_2O$, TlOAc, $TlNO_3$, $Tl(OAc)_3$, $Tl_2O_3$ or TlI.

7. A process according to claim 1, wherein there are at least 6.75 mols alcohol per mol of alkylene oxide.

8. A process according to claim 7, wherein there are 6.75 to 22.2 mols of alcohol per mol of alkylene oxide.

9. A process according to claim 1, wherein there are 1 to 20 mols of alcohol per mol of alkylene oxide.

* * * * *

UNITED STATES PATENT AND TRADEMARK OFFICE
CERTIFICATE OF CORRECTION

PATENT NO. : 4,434,105

DATED : February 28, 1984

INVENTOR(S) : Hans-Josef Buysch et al

It is certified that error appears in the above-identified patent and that said Letters Patent is hereby corrected as shown below:

| | |
|---|---|
| Col. 2, line 22,23 | Delete "tetramethylammonium" and substitute --tetraethylammonium-- |
| Col. 2, line 45 | After "($OCH_3$)" delete "Hd 2" and substitute --$_2$-- |
| Col. 2, line 48 | Delete "TlT" and substitute --TlI-- |
| Col. 2, line 51 | Delete "$Co_3$" and substitute --$CO_3$-- |
| Col. 5, line 27 | Delete "EXAMPE" and substitute --EXAMPLE-- |
| Col 6, line 58 | Delete "22.2" and substitute --22.3-- |

Signed and Sealed this

Seventeenth Day of July 1984

[SEAL]

Attest:

GERALD J. MOSSINGHOFF

Attesting Officer

Commissioner of Patents and Trademarks